(12) United States Patent
Gresham et al.

(10) Patent No.: US 6,809,313 B1
(45) Date of Patent: Oct. 26, 2004

(54) MICRO FARADAY-ELEMENT ARRAY DETECTOR FOR ION MOBILITY SPECTROSCOPY

(75) Inventors: Christopher A. Gresham, Albuquerque, NM (US); Phillip J. Rodacy, Albuquerque, NM (US); M. Bonner Denton, Tucson, AZ (US); Roger Sperline, Tucson, AZ (US)

(73) Assignee: Sandia Corporation, Albuquerque, NM (US)

( * ) Notice: Subject to any disclaimer, the term of this patent is extended or adjusted under 35 U.S.C. 154(b) by 17 days.

(21) Appl. No.: 10/390,507

(22) Filed: Mar. 17, 2003

(51) Int. Cl.[7] ............................................... H01J 49/40

(52) U.S. Cl. ......................... 250/287; 250/283; 250/397

(58) Field of Search ................................ 250/287, 283, 250/397

(56) References Cited

U.S. PATENT DOCUMENTS

| | | | | |
|---|---|---|---|---|
| 4,868,902 A | | 9/1989 | Sato ........................... | 250/332 |
| 5,386,115 A | | 1/1995 | Freidhoff et al. ........... | 250/281 |
| 5,455,417 A | * | 10/1995 | Sacristan .................... | 250/287 |
| 5,602,511 A | | 2/1997 | Woodaway ................. | 330/282 |
| 5,965,882 A | | 10/1999 | Megerle et al. ............. | 250/287 |
| 6,180,942 B1 | | 1/2001 | Tracy et al. ................. | 250/299 |
| 6,480,278 B1 | | 11/2002 | Fuerstenau et al. ......... | 356/394 |
| 6,630,663 B2 | * | 10/2003 | Murphy et al. ............. | 250/286 |

OTHER PUBLICATIONS

"Ion Mobility Spectrometry"; http://ims.isas–dortmund.de/ims/ims.html.

"Infra–red Imaging and Spectroscopy with Hawaii and Picnic Arrays", Kenworthy, Ellis and Aragon–Salamanca; http://www.ast.cam.ac.uk/~rgm/scratch/cirsi/SPIE_3354_1998_02_01.htm.

"Summary White Paper", Fuerstenau; Jet Propulsion Laboratory; In–situ Technology Group.

"Output characteristics of stacked CMOS–type active pixel sensor for charged particles", Nagashima, Kunihiro, Takayanagi, Nakamura, Kosaka and Yurimoto; 2001;31:131–137.

*Micromachined Faraday cup array using deep reactive ion etching.* </cgi–bin/w3ydkhgw?qryFPAh0a4.b:2002–7202633>. Darling, R.B.; Scheidemann, A.A., Bhat, K.N.; Chen, T. –C. Source: *Sensors and Actuators A (Physical)*; Jan. 1, 2002; vol.A95, No. 2–3, p. 84–93.

* cited by examiner

*Primary Examiner*—Jack I. Berman
(74) *Attorney, Agent, or Firm*—Elmer A. Klavetter

(57) ABSTRACT

An ion mobility spectrometer includes a drift tube having a collecting surface covering a collecting area at one end of the tube. The surface comprises a plurality of closely spaced conductive elements on a non-conductive substrate, each conductive element being electrically insulated from each other element. A plurality of capacitive transimpedance amplifiers (CTIA) adjacent the collecting surface are electrically connected to the plurality of elements, so charge from an ion striking an element is transferred to the capacitor of the connected CTIA. A controller counts the charge on the capacitors over a period of time.

7 Claims, 3 Drawing Sheets

MICRO FARADAY-ELEMENT ARRAY DETECTOR FOR ION MOBILITY SPECTROSCOPY

The United States Government has rights in this invention pursuant to Department of Energy Contract No. DE-AC04-94AL85000 with Sandia Corporation.

CROSS REFERENCE TO RELATED APPLICATIONS (Not Applicable)

BACKGROUND OF THE INVENTION

The rapid identification of explosives, explosive residues, chemical agents, airborne toxins, and other volatile organic compounds has undergone a revolution in recent years by the progress made in the field of ion mobility instruments. Despite the transformation that has occurred in ion mobility spectrometry, the full potential of the technique has not yet been realized. This is primarily due to the ion detection systems employed in mobility spectrometers.

FIG. 1 shows a typical ion mobility spectrometer (IMS) 5 to include an ionization reaction chamber 10 in which gas 7 enters and is ionized, an ion drift chamber 20 connected in series with reaction chamber 10 through an ion/molecular injection shutter 12, and a collector plate 16. In operation, a carrier gas transports gases or vapor from material to be analyzed into the reaction chamber 10, where it is ionized by an ionization source. Most of the resulting ions are from the carrier gas molecules, and multiple collisions occur between ionized species and the analyte molecules. These collisions transfer ion charge to the analyte molecules.

For improved resolution, an aperture grid 17 serves as a guard for the collector plate 16 to prevent precharging of the collector due to charging by the approaching "ion packet". This grid also helps maintain the uniformity of the electric field responsible for motion of the ions. Periodically, the ion shutter 12 (a charged grid) is opened to allow a pulse of ions into the drift chamber 15. The time of arrival of each ion species at the collector plate 16 is determined by the mobility of the ions in a non-ionizing gas filling the drift chamber 15. The quantity of ions collected at collector plate 16 as a function of drift time is recorded as a current by a microprocessor.

The current state-of-the-art detection limit using a Faraday cup is around 6 thousand ions per second in the most expensive isotope ratio mass spectrometers. This corresponds to 1 femtoamp of current. It takes very sophisticated electronics to measure this small current with any certainty. The direct current measuring devices used in prior art ion mobility spectrometers are able to only measure currents in the picoamp range. This raises the detection limit of the device three orders of magnitude to over 6 million ions per second. This limitation requires high ion fluxes that cause poor linear dynamic range, false positive responses, and numerous other problems.

Because the use of electron multipliers at atmospheric pressures is problematic, researchers have attempted direct electrometer measurements on the very small signals produced by ion packets. Two general methods have been employed.

In the first method, electrometer measurements use amplifiers with extremely high input impedance to measure the voltage resulting from the flow of current through high-precision high-value resistors (typically $10^{10}$ to $10^{12} \Omega$) or from the accumulation of charge on a small input capacitor. Limitations on the smallest detectable current by such methods arise from noise effects in the input resistor and from the variable capacitance of the ion collector and cables inherent in the device. High-value input resistors are typically used to produce voltages from the small ion currents. For a $10^{12} \Omega$ input resistor, the thermal noise arising from thermally induced charge fluctuations amounts to about ±1 femtoamp at room temperature. The current is determined from a voltage change at a given time. The noise in the rate-of-charge measurement arises from voltage fluctuations in the amplifier. These fluctuations cause relatively high detection limits.

The other method to determine the charge is to measure the change in a capacitor. The same noise fluctuations are involved in this method, and produce similar detection limits. Furthermore, detection limits of several thousand ions per second have not yet been realized for portable ion mobility spectrometers using the existing technology.

A whole new generation of promising ion detectors has been developed based on infrared multiplexer arrays used for night vision and in astronomy. Detection of infrared radiation requires the use of materials with lower band-gaps than silicon devices can offer. The infrared-active materials used are, however, not suitable for the readout multiplexer electronics required for ion detection. Infrared focal plane detectors are often constructed by placing infrared active materials on top of silicon readout multiplexers. These "stacked systems" are capable of reading extremely low levels of charge with exceptionally low read-out noise and low dark currents. An entire generation of ion detectors has been realized from combining the technologies developed for CCD's, infrared multiplexers, and Faraday ion detection. The result is the micro-Faraday element array capable of low charge detection with ultra-low noise characteristics.

U.S. Pat. No. 6,180,942 of D. Tracy et al. discloses at FIG. 4, an array of ion detectors having a plurality of pickup electrodes separated from a substrate by an insulating layer. Each electrode has associated therewith an undefined 'charge storage circuit 38' where stored voltage is measured before and after sampling. After correction for thermal noise, a multiplexing circuit reads the outputs of the charge storage circuits.

U.S. Pat. No. 6,480,278 of S. Fuerstenau et al. discloses a device for measuring the charge on individual charged particles. The device has a plurality of very small collector plates for measuring charges on droplets, each plate being connected to a CMOS device that includes sample and hold capacitors. The patent indicates a charge transimpedance amplifier may be utilized, but does not show such an embodiment. The patent also stores charge on the element, which means the device is adversely affected by nearby capacitance.

U.S. Pat. No. 5,602,511 of J. Woolaway discloses several capacitive transimpedance amplifiers. FIG. 3 of this patent discloses a CTIA that may be used for signals of different amplitudes by controlling the amount of feedback capacitance.

SUMMARY OF THE INVENTION

It is an object of this invention to provide a novel ion collection/detection system for an IMS.

To achieve the foregoing and other objects, and in accordance with the purpose of the present invention, as embodied and broadly described herein, is an IMS comprising a drift tube for the passage of ions toward an ion collecting surface covering a collecting area at one end of the tube, the surface comprising a plurality of closely spaced conductive elements on a non-conductive substrate, each conductive element being electrically insulated from each other element. A plurality of CTIAs are adjacent the collecting surface, each CTIA having a high impedance input and a charge storage capacitor. Each of the elements is electrically connected to an input of one of said CTIAs, so charge from an ion striking the element is transferred to the capacitor of the connected CTIA. Control means are provided for determining the charge on the capacitors over a period of time.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 1:
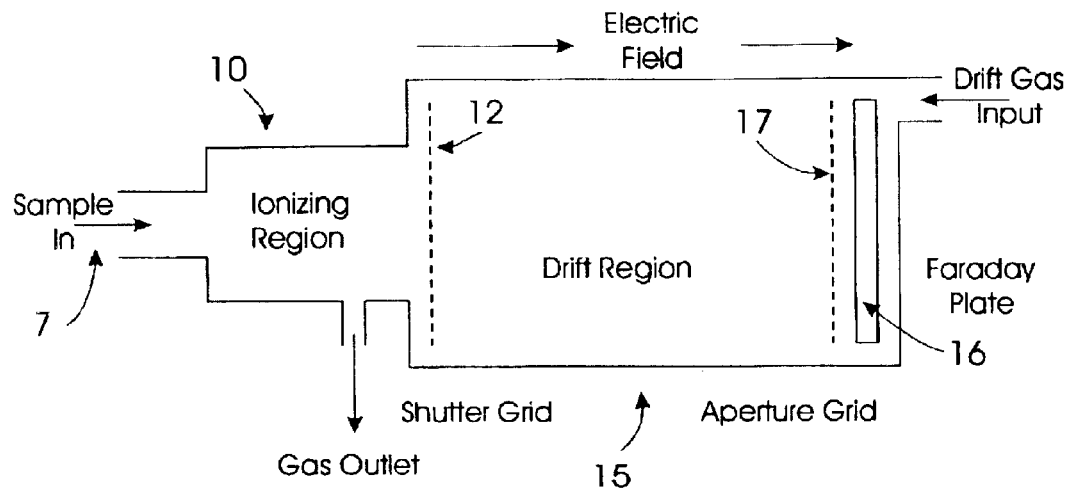
FIG. 1 shows the basic construction of a prior art ion mobility spectrometer.
Figure 2:
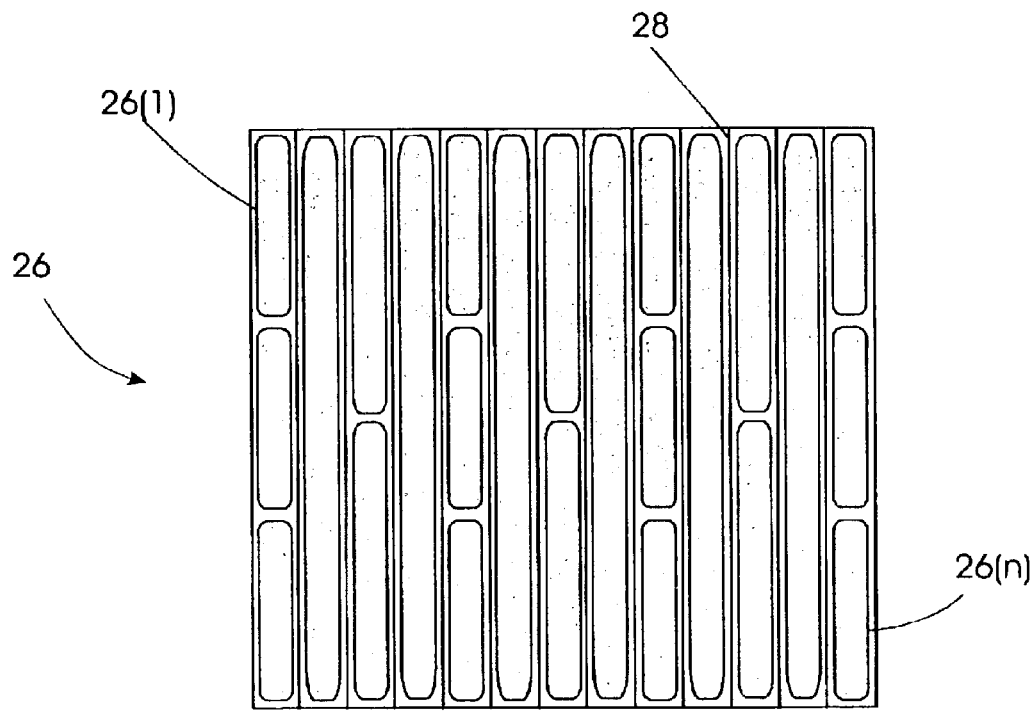
FIG. 2 shows a typical array of Faraday electrodes elements for use in an IMS.

The typical prior art Faraday plate 16 for an IMS is an electrically conductive plate. As shown in FIG. 2 and practiced in this invention, the charge collector 26 comprises n small, adjacent electrically conductive electrode elements 26(1)–26(n) arranged on a substrate. Any one of these elements is designated 26(i).

The collection elements may be produced by standard lithographic techniques and made extremely small (down to 10 $\mu$m), and closely spaced (10 $\mu$m) in large numbers. The small physical size of the collection elements and associated measurement circuitry results in dramatically reduced input capacitance and allows the accumulation of charge on femptofarad feedback capacitors rather than on the tens-of-picofarad capacitors typical of an electrometer system. Lowered capacitance produces a corresponding improvement in sensitivity. The signal required to overcome the limiting amplifier noise drops from thousands of electrons per second to only a relatively few electrons in a given integration period. The array detector device described herein does not measure current, but measures charge. With this arrangement, signals from a very low flux of positive or negative ions can, therefore, be reproducibly and quantitatively measured.

For the embodiment shown in FIG. 2, each of 24 elements had a width of 145 $\mu$m and a length of one of 5, 2.45, and 1.6 mm. The multiple lengths were provided in the test embodiment to enable studies to see what length might be preferable for which application. Each element row was separated from the next row by a grounded guard electrode that was 10 $\mu$m wide and as high as the elements to minimize inter-element capacitance. Each finger was made from 7 $\mu$m thick gold over a 1 $\mu$m thick buffer layer of titanium deposited on a silica-glass substrate.

It should be understood that the collection elements 26(i) could take many shapes, arrangements, and numbers. For example, all elements could be equally sized an arranged either in parallel rows or a spiral arrangement. In another test, eleven electrodes 5 mm long were connected together to provide a total electrode area of 7.98 mm$^2$. Similarly, the guard electrodes may or may not be present.

Figure 3:
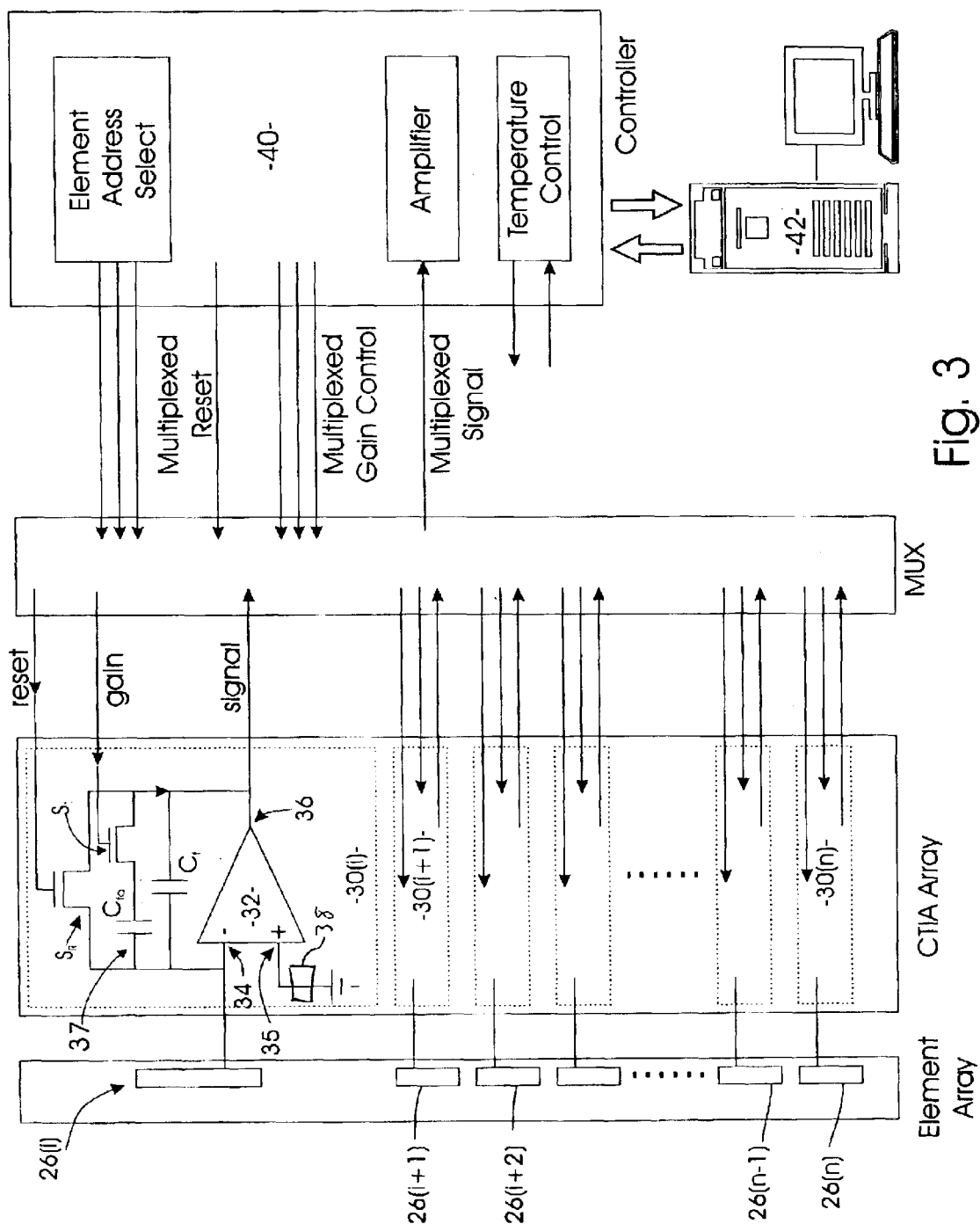
FIG. 3 shows a schematic view of the system.

Each element 26(i) is connected to a dedicated capacitive transimpedance amplifier (CTIA) 30(i) as schematically shown in FIG. 3. A CTIA is a conventional item well known in the detecting art that is typically embodied in an integrated circuit. For a preferred embodiment of this invention, a plurality of CTIA 30(n) are in an integrated circuit package, and the element array 26 is mounted atop the CTIA package with a short conductive wire or "bump bond" extending from each element 26(i) to a different CTIA 30(i) input 34. As will be recognized by those skilled in the art, thermal insulation may be required between the element array and the CTIA package.

Each CTIA 30(i) typically includes an operational amplifier 32 having a negative input 34 connected to an clement 26(i) and a positive input 35 connected to an array offset bias voltage 38 which permits either positive or negative ions to be processed. The output 36 of amplifier 32 is fed back to the negative input 34 through feedback capacitor $C_f$, which has a value on the order of 36 fF for the small elements utilized in this invention. A normally open reset switch $S_R$ is in parallel with feedback capacitor $C_f$. Optionally, each CTIA 30 may be provided with controllable gain by utilizing one or more controllable feedback circuits 37 including a small capacitor $C_{fa}$ in series with a switch $S_1$. Each amplifier output is directed to an input of multiplexer 38 that is controlled by controller 40 as described hereinafter. The description of multiplexer 38, controller 40 and computer 42 is intended to represent the functions performed on the CTIA array. The hardware and software required to implement these functions is an obvious matter of design to those of ordinary skill in the art.

The CTIA of FIG. 3 operates as follows: Each element is maintained at a constant potential, which means that collection efficiency stays constant. As charged ions strike an element 26(i), the output of amplifier 32 increases, which pulls the charge from element 26(i) onto feedback capacitor $C_f$. Because q=vC and the potential at input 34 is fixed, a voltage then appears across feedback capacitor $C_f$ at output 36 that is a function of the known capacitance of $C_f$ and the number of ions which struck element 26-i. This output voltage remains until switch $S_R$ is closed to short out $C_f$ and discharge element 26(i). To provide for the "random access integration" described below, an additional feature of the multiplexer system would allow random resetting of individual CTIA amplifiers through switches $S_R$.

The gain of CTIA 30(i) is varied by controller 40 providing a signal to close switch $S_1$ and place capacitor $C_{fa}$ in parallel with capacitor $C_f$. More than one capacitor may be connected in parallel with $C_f$ in this manner.

Multiplexer 38 successively connects each output voltage 36 to a controller 40 where the output voltages are summed to provide a total voltage that is indicative of the total charge on all elements over the measurement period. This voltage is equivalent to the output that would be attained from a single conventional Faraday plate in an IMS. Alternatively, voltages from individual elements may be examined to form an "image" of the spacial distribution of the ion beam striking the element array.

Controller 40 can provide several and varied read-out modes for this invention. The background charge can be separately determined and subtracted from measurements, as in normal MUX operation. To do this, switch $S_R$ is closed and opened to reset the charge, and a read operation is performed to determine the "background" charge. An exposure is then initiated and a second read operation is performed to determine the "ion charge". The entire cycle can be repeated. The device can also be read in a manner similar to that of charge-injection devices (CIDs). Using the known technique of "random access integration" (RAI), the charge integration time between destructive read outs is varied under computer control so that detector elements receiving low ion fluxes are integrated for a longer period of time. This, in effect, optimizes the integration time for each individual detector element. The additional desirable ability to perform non-destructive readouts ("NDROs") has allowed CIDs used in optical emission spectroscopy to be operated with a linear dynamic range exceeding ten orders of magnitude. In this mode, the device is reset after many readouts, rather than between readouts For this application, the multiple NDRO readouts will reduce the noise by the square root of the number of times a charge is read as well as allowing increased linear dynamic range.

Preliminary results for the non-optimized detector boast a detection limit on the order of 100 total ions. It is estimated that the detection limit of 10 ions or lower can be achieved. Because the measurements for the ion mobility applications will be taken on the millisecond to microsecond time-scale, the background signal and dark current produced in a measurement will be much less than the read-noise. This should provide detection limits comparable with that of vacuum mass spectroscopy on the time scale needed for ion mobility measurements.

For a feasibility study, two sets of results were compared. The first set of results was obtained using a conventional IMS PCP 110 with traditional Faraday plate detector for explosive analysis. The same IMS unit was then modified by removing the traditional Faraday plate and replacing it with the micro-Faraday array detector described above. Only about 25% of the array elements were in the ion path, as the array was designed for high vacuum, mass spectral analysis and was not optimized for use with an existing IMS detector.

In addition, the array was designed to run at 233 K, so the sample inlet and drift region were held at 80° C. to prevent thermal shock damage to the detector array. For this study, the detector temperature was held between 250 and 260 K. Sample introduction from the liquid to the vapor phase was accomplished using a flash tungsten filament coated with a given amount of HMX explosive standard. The flash current applied through the filament was 1.1 amps. The drift tube electrode stack was held at a potential of 1300 V DC and the gating used was a 500 μs pulse width at 10 Hz. The IMS was operated in the negative ion mode using nitrogen as the carrier and drift gas with methylene chloride comprising the reactant ion gas via a permeation tube.

Figure 4A:
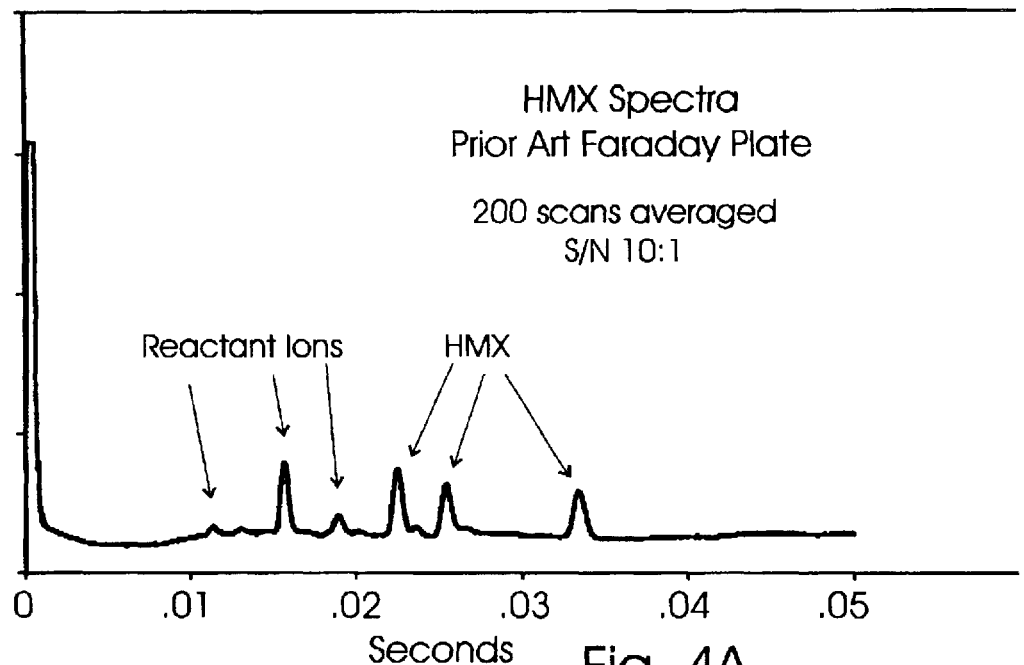
FIGS. 4A and 4B show, respectively, measurements by IMS using a prior art electrode and the elements of the invention.

The signal to noise for a single scan using the traditional Faraday plate detector is approximately 2:1. In order to improve the signal to noise, the same set of experiments was performed using 200 averaged scans. The signal to noise was then improved to approximately 10:1 as shown in FIG. 4A.

Figure 4B:
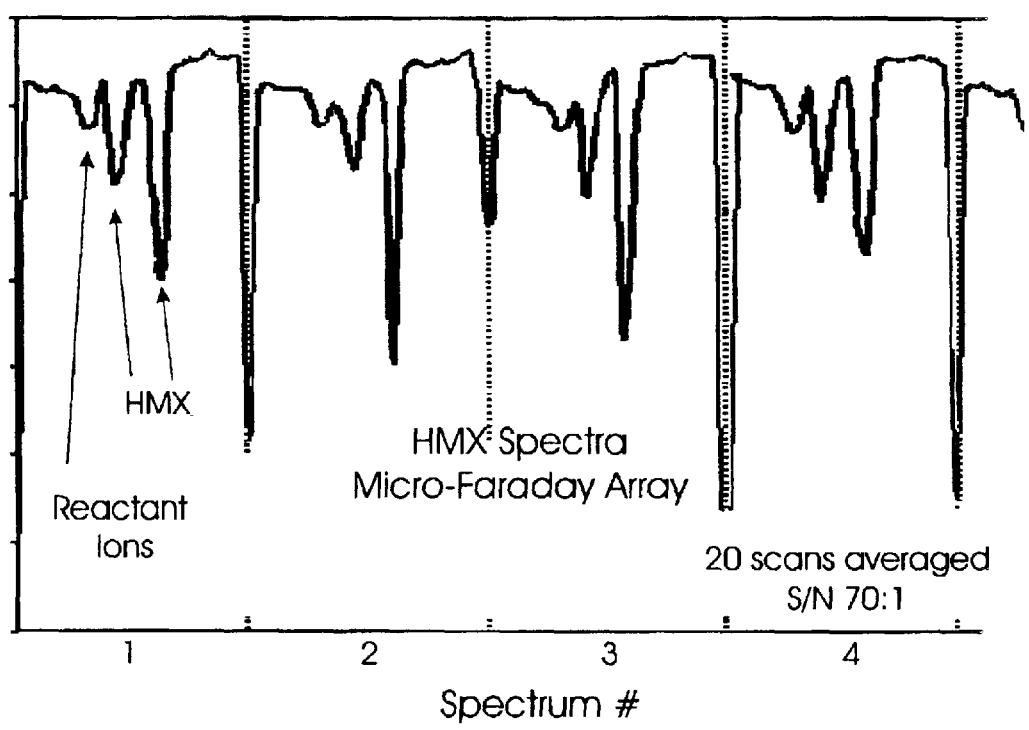

When the test was repeated with the micro-Faraday array, it became readily apparent that there was a loss of resolution using the modified IMS. This loss of resolution was expected, because the drift tube was operated at sub-optimal voltage to compensate for the relatively long sampling interval of this prototype system. As shown in FIG. 4B, several other differences are easily observed. The original array controller timing and readout scheme produced multiple averaged spectral displays that are of no consequence for this feasibility study. Further examination, however, revealed that the signal to noise of just 20 averaged scans is 70:1. Extrapolation of those results to 200 scans would yield a ratio on the order of 200:1.

The results obtained during this feasibility study using a non-optimized micro-Faraday array detector coupled to a conventional IMS reveal a significant increase in sensitivity for explosive detection. The limit of detection for HMX using the PCP 110 IMS with traditional Faraday plate detector was determined to be $2\times10^{-12}$ grams. The detection limit obtained using this non-optimized micro-Faraday array detector was determined to be $6\times10^{-15}$ grams. These results represent a three order of magnitude increase in sensitivity without the advantage of utilizing an optimized IMS coupled to a dedicated micro-Faraday array detector.

One of the reasons for the dramatic results noted above is that the capacitance between each element 26-i and neighboring structure such as other elements 26 and the aperture grid 17 is much smaller than the capacitance between a large plate 16 and neighboring structure. Another reason is that a Faraday plate is a direct read device where thermal noise effects of input resistors cause voltage fluctuations in the amplifier, and the plate requires thousands of ions/second to develop a signal. The charge-coupled elements 26(i) require only tens of ions/second and can be read non-destructively.

It should be apparent that there are many modifications possible with this invention, as long as the concept of using a plurality of small collector plates with a plurality of CTIAs for storing the charge on each plate is followed. For example, several elements could be connected to one CTIA, with the several elements functioning as one larger element. In addition, while this embodiment has been disclosed with a drift tube, other drift regions, such as parallel plates in various configurations, may be utilized. It is intended that the scope of the invention the appended claims.

What is claimed is:

1. An ion mobility spectrometer (IMS) comprising:
   a drift region for the passage of ions toward an ion collecting surface covering a collecting area, said surface comprising a plurality of closely spaced conductive elements on a non-conductive substrate, each conductive element being electrically insulated from each other element, wherein said drift region is a drift tube and said ion collecting surface is at an end of said drift tube;
   a plurality of capacitive transimpedance amplifiers (CTIA) adjacent said collecting surface, each CTIA having a high impedance input and a charge storage capacitor, wherein each of said elements is electrically connected to an input of one of said CTIAs, and charge from an ion striking an element is transferred to said capacitor of said connected CTIA;
   control means for determining the charge on said capacitors over a period of time.

2. The IMS of claim 1 wherein each CTIA comprises an operational amplifier having two balanced inputs and a differencing output, said storage capacitor being connected across a negative input and said output; wherein the output voltage of said operational amplifier is proportional to the stored charge on said capacitor.

3. The IMS of claim 2 further comprising a normally open reset switch for controllably closing to discharge said storage capacitor.

4. The IMS of claim 3 wherein said reset switch is in parallel with said storage capacitor.

5. The IMS of claim 2 wherein said control means comprises:
- a multiplexer having a plurality of multiplexer inputs, each multiplexer input being electrically connected to a different one of said operational amplifier outputs, and a multiplexer output controllably connected to each multiplexer input; and
- a controller for summing the voltages applied to said multiplexer inputs.

6. The IMS of claim 5 wherein the gain of each CTIA is controllable.

7. The IMS of claim 6 wherein each operational amplifier has a second capacitor and a series switch in parallel with said storage capacitor, said series switch being closed by said controller to vary the gain of said CTIA.

* * * * *